(12) United States Patent
Zhou

(10) Patent No.: US 11,497,383 B2
(45) Date of Patent: Nov. 15, 2022

(54) PROTECTIVE SHEATH, HYSTEROSCOPE EQUIPPED THEREWITH, AND NEPHROSCOPE EQUIPPED WITH SAME

(71) Applicant: SHANGHAI ANQING MEDICAL INSTRUMENT CO., LTD., Shanghai (CN)

(72) Inventor: Zhenhua Zhou, Shanghai (CN)

(73) Assignee: SHANGHAI ANQING MEDICAL INSTRUMENT CO., LTD., Shanghai (CN)

(*) Notice: Subject to any disclaimer, the term of this patent is extended or adjusted under 35 U.S.C. 154(b) by 349 days.

(21) Appl. No.: 16/753,196

(22) PCT Filed: Oct. 20, 2017

(86) PCT No.: PCT/CN2017/106952
§ 371 (c)(1),
(2) Date: Apr. 2, 2020

(87) PCT Pub. No.: WO2019/075705
PCT Pub. Date: Apr. 25, 2019

(65) Prior Publication Data
US 2020/0260937 A1    Aug. 20, 2020

(51) Int. Cl.
*A61B 1/00* (2006.01)
*A61B 1/005* (2006.01)
(Continued)

(52) U.S. Cl.
CPC ........ *A61B 1/00142* (2013.01); *A61B 1/0052* (2013.01); *A61B 1/00068* (2013.01);
(Continued)

(58) Field of Classification Search
CPC ............ A61B 1/00068; A61B 1/00137; A61B 1/00142
See application file for complete search history.

(56) References Cited

U.S. PATENT DOCUMENTS 5,562,602 A * 10/1996 Yabe .................. A61B 1/05
600/125
5,733,243 A * 3/1998 Yabe .................. A61B 1/012
600/156

FOREIGN PATENT DOCUMENTS

CN          102384138 A     3/2012
CN          203571290 U     4/2014
(Continued)

*Primary Examiner* — Aaron B Fairchild
(74) *Attorney, Agent, or Firm* — Muncy, Geissler, Olds & Lowe, P.C.

(57) ABSTRACT

The present invention provides a protective sheath, a hysteroscope equipped therewith, and a nephroscope equipped with the same, used to prevent contaminants from contaminating electrical connecting lines connected to the endoscope. The protective sheath includes an inner sheath (1) and an outer sheath (2), which are sleeved together, the outer sheath (2) has a cylindrical structure, the inner sheath (1) includes a straight cylindrical portion and a bell mouth portion, the bell mouth portion is located on an insertion end side of the inner sheath (1), a side wall of the bell mouth portion is provided with a plurality of grooves extending from the bell mouth portion to the straight cylindrical portion, and a plurality of elastic sheets (12) are formed at the insertion end of the inner sheath (1); a connecting portion cooperating with a self-locking quick connector (7) is formed on the inner wall of each elastic sheet (12); and a hollow cavity is disposed between the inner sheath (1) and the outer sheath (2), and a compressed waterproof jacket (3) is disposed in the hollow cavity, one end of the waterproof jacket (3) is fixedly sheathed on the inner sheath (1), and the other end of the waterproof jacket (3) can be pulled through a non-insertion end of the protective sheath. The protective sheath is lightweight, compact, and easy to operate. The protective sheath effectively protects the electrical connecting lines from being contaminated during use, thereby (Continued)

preventing short circuit, contamination and other situations, furthermore, the protective sheath is low in production cost and can be used as a disposable medical device.

23 Claims, 4 Drawing Sheets

(51) Int. Cl.
　　*A61B 1/04*　　　　(2006.01)
　　*A61B 1/06*　　　　(2006.01)
　　*A61B 1/303*　　　(2006.01)
　　*A61B 1/05*　　　　(2006.01)
　　*A61B 1/307*　　　(2006.01)
(52) U.S. Cl.
　　CPC .......... *A61B 1/00137* (2013.01); *A61B 1/042* (2013.01); *A61B 1/05* (2013.01); *A61B 1/0669* (2013.01); *A61B 1/0676* (2013.01); *A61B 1/303* (2013.01); *A61B 1/307* (2013.01); *A61B 2560/0285* (2013.01)

(56) References Cited

FOREIGN PATENT DOCUMENTS

| CN | 205215143 U | 5/2016 |
| CN | 105962877 A | 9/2016 |
| CN | 107049207 A | 8/2017 |
| CN | 107811598 A | 3/2018 |
| JP | 0998938 A | 4/1997 |

\* cited by examiner

PROTECTIVE SHEATH, HYSTEROSCOPE EQUIPPED THEREWITH, AND NEPHROSCOPE EQUIPPED WITH SAME

FIELD OF THE INVENTION

The present invention relates to the field of medical equipment, and in particular to a protective sheath, a hysteroscope equipped therewith, and a use method of the protective sheath.

BACKGROUND OF THE INVENTION

An endoscope is a kind of light source endoscope that is mainly used for in vivo inspection and treatment of human body. The endoscope enters the human body via the front of a lens body, it becomes the preferred inspection method for internal lesions of the human body because of intuitive and accurate. However, in the prior art, during the in vivo inspection of a body of the patient, it is usually necessary to stretch the endoscope into the body of the patient at first to enter the human body, so as to observe the patient, after a lesion is found, the endoscope is taken out to treat the patient, or, the endoscope is reserved in the body of the patient, and then a treatment instrument is stretches into the body of the patient to treat the patient. During the diagnosis and treatment, it is usually necessary to inject normal saline into the body of the patient to expand the uterus, the liquid in the body of the patient will flow out from the body to pollute the endoscope after the expansion of the uterus. In use, the endoscope is often connected to a display by an electrical connecting line, and the dirt flowing out from the body of the patient is extremely likely to cause pollution to the electrical connecting line and is also prone to a short circuit.

An existing first embodiment discloses an endoscope, including a mirror sheath and sight glass, the sight glass is disposed in the mirror sheath, an inner sheath and an outer sheath are disposed at the outside of the mirror sheath, a water inlet and a water outlet are disposed on the outer sheath, an operation electrode is disposed between the sight glass and the inner sheath, the operation electrode is connected with an operation handle disposed at the outside of the mirror sheath, a slide block is movably disposed at the outside of the sight glass, a suction tube for adsorbing tissues is arranged between the sight glass and the inner sheath, and a baffle for opening and closing the port of the suction tube is movably disposed in the suction tube.

An existing second embodiment discloses an endoscope, including insertion tube, a camera, a light source and a display portion, the camera and the light source are disposed at an insertion end of the insertion tube, a display portion is disposed at a rear end of the insertion tube, the display portion is connected with the camera, the endoscope further includes: a ring removing device, disposed in the insertion tube and capable of protruding from the insertion tube from the insertion end of the insertion tube or retracting into the insertion tube; and an extension and retraction-clamping control device, connected with the ring removing device, and capable of controlling the ring removing device to extend out from the insertion end of the insertion tube or retract into the insertion tube, and controlling the ring removing device to clamp a contraceptive ring when the ring removing device extends out.

An existing third embodiment discloses a medical surgical mirror, and particularly relates to an endoscope applied to gynecological minimally invasive surgery. The endoscope includes a mirror tube, an objective lens is disposed at one end of the mirror tube, the other end of the mirror tube is connected with a main body, the mirror tube includes a bent segment and a straight line segment, the bent segment is provided with an objective lens and a prism, the straight line segment is connected with the main body, an imaging channel and a working channel, parallel to each other, are disposed in the mirror tube, the imaging channel and the working channel pass through the entire mirror tube, the objective lens is located at the end portion of the imaging channel, a prism and an image transmission optical fiber are further disposed in the imaging channel, a light transmitting bundle interface is disposed on the main body, a light transmitting bundle is disposed in the light transmitting bundle interface, and the light transmitting bundle is located in the mirror tube. The utility model provides an endoscope, which is simple in structure, convenient to operate and accurate to locate, and can cooperate with different instruments for use; and the technical problems that the endoscope in the prior art is complicated in structure and inconvenient to operate, and that cannot cooperate with different instruments for use are solved.

An existing fourth embodiment discloses a medical device, specifically an endoscope water leakage prevention device, including a transparent film that can be attached to the vulva, an endoscope operation support is disposed at the central position of the transparent film, an operation hole is formed in the middle of the operation support, a rubber plug for sealing the hole is cooperatively disposed in the operation hole, and after the rubber plug is hermetically sheathed on an endoscope, the endoscope can pass through the operation support to stretch into the uterine cavity.

The endoscope is more complicated to operate in actual use, and can only prevent the liquid from flowing out from the patient to a certain extent, so that the safety and reliability are relatively low.

In the prior art taking the above-mentioned endoscope as an example, the electrical connecting line is inevitably contaminated by the dirt flowing out from the body of the patient, which is not only prone to short-circuit and other dangers to damage the electrical appliances, and also easily contaminates the clothes of the user. In addition, because the electrical connecting line is not easy to sterilize, it is prone to secondary pollution.

SUMMARY OF THE INVENTION

The present invention discloses a protective sheath, including an inner sheath and an outer sheath, which are sleeved together, the outer sheath has a cylindrical structure, the inner sheath includes a straight cylindrical portion and a bell mouth portion, the bell mouth portion is located on an insertion end side of the inner sheath, a side wall of the bell mouth portion is provided with a plurality of grooves extending from the bell mouth portion to the straight cylindrical portion, and a plurality of elastic sheets are formed at the insertion end of the inner sheath; the straight cylindrical portion is located on a non-insertion end side of the inner sheath;

a hollow cavity is disposed between the inner sheath and the outer sheath, and a compressed waterproof jacket is disposed in the hollow cavity, the waterproof jacket has a tubular structure, one end of the waterproof jacket is fixedly sheathed on the inner sheath, the other end of the waterproof jacket can be pulled out from a non-insertion end of the protective sheath, so that the waterproof jacket is pulled out from the hollow cavity.

Preferably, the number of the elastic sheets is an even number.

Further, two adjacent elastic sheets are regarded as an elastic sheet group, one elastic sheet in the elastic sheet group is formed with a protrusion on an outer surface of the bell mouth portion, a groove is formed in a position corresponding to the protrusion on an inner surface of the outer sheath, and when the inner sheath is completely sheathed in the outer sheath, the protrusion is inserted into the groove.

Preferably, a connecting portion is formed on the other elastic sheet in the elastic sheet group, the connecting portion is located at the boundary between the straight cylindrical portion and the bell mouth portion, and the connecting portion is a convex portion protruding toward the axis of the inner sheath.

Preferably, one end of the waterproof jacket is fixed at the non-insertion end of the inner sheath.

Preferably, the bell mouth portion of the inner sheath is provided with an annular sealing ring to cover the top of the bell mouth portion.

Preferably, the protective sheath is provided with an unsealing portion, the unsealing portion is fixedly connected with the waterproof jacket, and the waterproof jacket can be pulled out from the hollow cavity by pulling the unsealing portion.

The protective sheath can effectively protect the electrical connecting line, prevent the electrical connecting line from being polluted by the dirt. It has a simple structure, be convenient to use, and does not cause economic pressure on the patient.

The present invention further provides a hysteroscope, including an insertion tube and a handle connected with a non-insertion end of the insertion tube, a camera module seat is fixedly disposed at an insertion end of the insertion tube, a camera and a light source are disposed in the camera module seat, and the camera and the light source are electrically connected with a self-locking quick connector disposed on the handle, and the protective sheath as described above is sheathed at the outside of the self-locking quick connector;

the handle takes the shape of a gun, the handle includes a connecting portion connected with the insertion tube and a gripping portion, and a first instrument mouth is disposed at an upper end of the connecting portion; a water inlet base and a water outlet base are disposed at a lower end of the gripping portion, and valve switches are respectively disposed on the water inlet base and the water outlet base;

a water inlet tube is disposed in the water inlet base, a water outlet tube is disposed in the water outlet base, the water inlet tube and the water outlet tube are both disposed in the insertion tube and extend along the insertion tube, one end of the water inlet tube and one end of the water outlet tube are both disposed on an end face of the insertion end of the camera module seat, and the other end of the water inlet tube and the other end of the water outlet tube respectively communicate with the water inlet base and the water outlet base; and a first instrument tube is also disposed in the insertion tube, an instrument outlet of the first instrument tube is disposed on the end face of the insertion end of the camera module seat, and an instrument inlet of the first instrument tube communicates with the first instrument mouth; and a water retaining ring is sheathed at the outside of the non-insertion end of the insertion tube, and the water retaining ring can move along the axis of the insertion tube.

Preferably, a convex portion is formed on the inner wall of the inner sheath of the protective sheath, a concave portion is disposed at a corresponding position on the outer surface of the self-locking quick connector, and the convex portion can be clamped in the concave portion.

The present invention further provides a nephroscope, including an insertion tube and a handle connected with a non-insertion end of the insertion tube, a tip head is fixedly disposed at a front end of the insertion tube, and the tip head is provided with an instrument tube mounting channel for inserting an instrument tube and a camera module mounting channel for mounting a camera module; the handle is connected to a tail end of the insertion tube through a rigid connecting piece, a rear end of the handle is provided with a self-locking quick connector for connecting a display device, and the protective sheath as described above is sheathed at the outside of the self-locking quick connector;

wherein, a front end face of the tip head of the insertion tube is provided with an instrument outlet, a rear end face of the handle is provided with a corresponding instrument inlet, the instrument inlet is inserted into the handle to communicate with an instrument tube in the insertion tube, an acute included angle between the section axis of the instrument inlet and the section axis of an instrument catheter in the handle is less than 15 degrees.

Preferably, a convex portion is formed on the inner wall of the inner sheath of the protective sheath, a concave portion is disposed at a corresponding position on the outer surface of the self-locking quick connector, and the convex portion can be clamped in the concave portion.

The present invention further provides a use method of the protective sheath, including the following steps:

1. making the insertion end of the protective sheath face to the self-locking quick connector of the hysteroscope or the nephroscope, and sheathing the same at the outside of the self-locking quick connector, until the connecting portion is clamped with the self-locking quick connector;

2. forming a plugging connection between an electric transmission line and the self-locking quick connector; and 3. holding the unsealing portion to pull out the waterproof jacket to sheath the electric transmission line.

As mentioned above, the protective sheath and the hysteroscope with the protective sheath involved in the present invention are simple in structure, light in weight, small in volume and easy to operate, and can effectively protect the electrical connecting lines from being contaminated during use, thereby preventing short circuit, contamination and other situations, furthermore, the protective sheath and the hysteroscope are low in production costs and can be used as disposable medical devices.

In order to make the above contents of the present invention more comprehensible, preferred embodiments are listed below and are described in detail below in combination with the drawings.

BRIEF DESCRIPTION OF THE DRAWINGS

The present invention is described below with reference to the drawings.

FIG. 1-2 is a schematic diagram of an overall structure of a protective sheath with a sealing ring of the present invention;

FIG. 2-1 is a sectional view of FIG. 1;

FIG. 2-2 is a sectional view of FIG. 1-2;

DETAILED DESCRIPTION OF THE EMBODIMENTS

The implementation manner of the present invention is illustrated by specific embodiments below. Those skilled in the art can easily understand other advantages and effects of the present invention from the contents disclosed in the specification.

Figure 1:
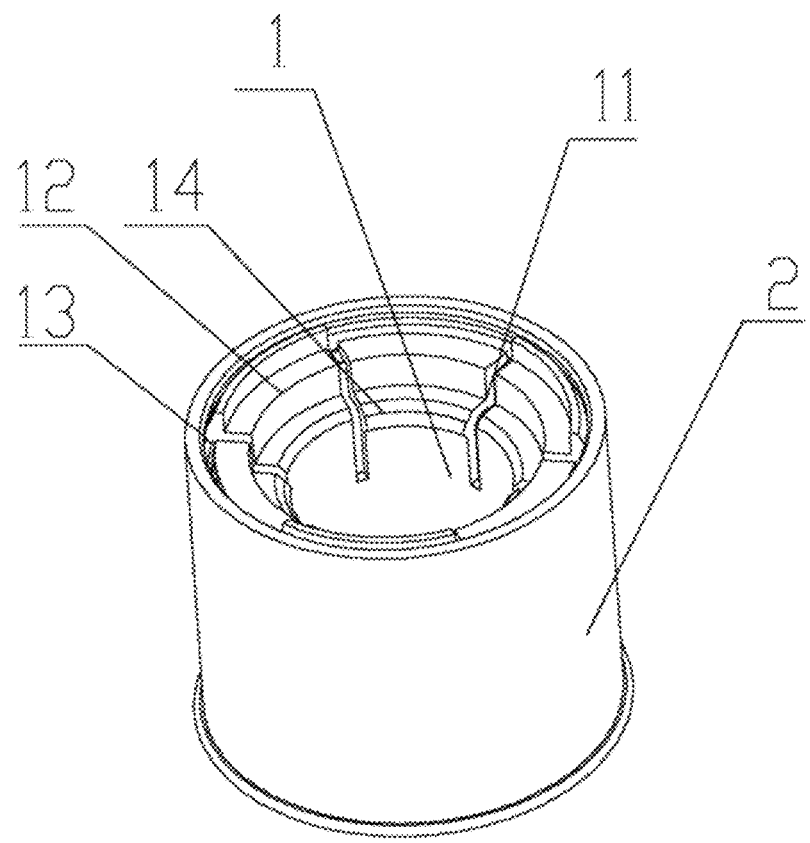
FIG. 1-1 is a schematic diagram of an overall structure of a protective sheath of the present invention.
Figures 1, 2:
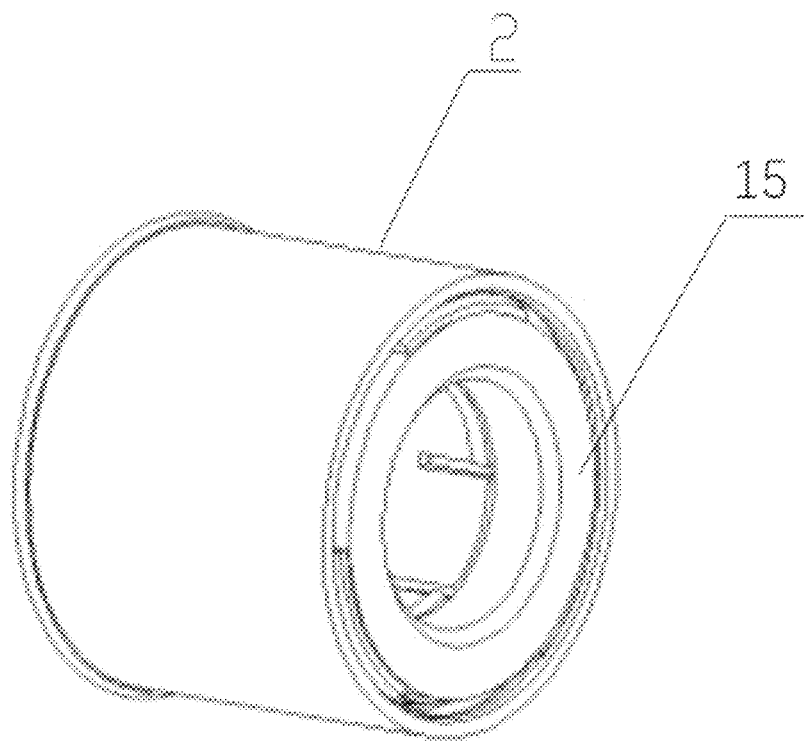
Figures 1, 2:
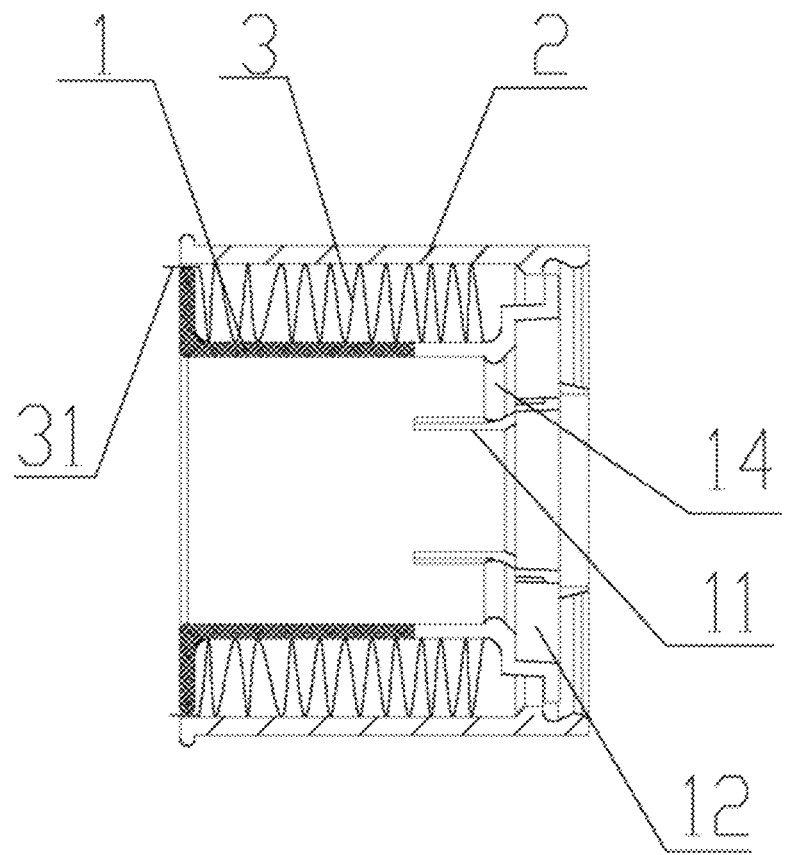
Figure 2:
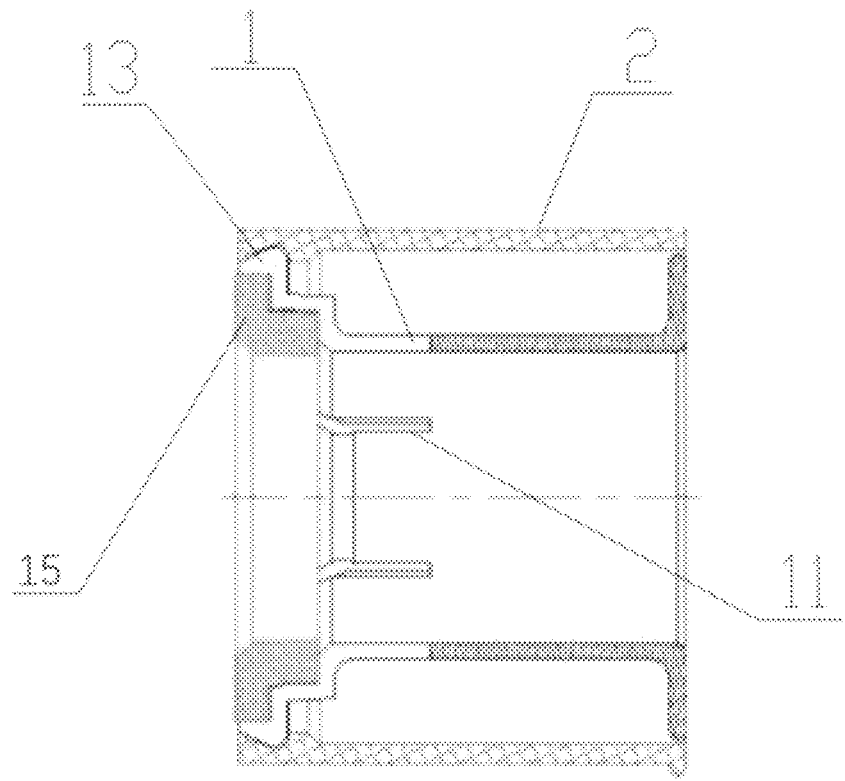

As shown in FIG. 1-1, FIG. 1-2, FIG. 2-1 and FIG. 2-2, the present invention relates to a protective sheath for preventing an electrical connecting line connected with endoscopes such as a hysteroscope, a nephroscope from being contaminated by dirt. The protective sheath includes an inner sheath 1 and an outer sheath 2, which are sleeved together, a waterproof jacket 3 is disposed in a hollow cavity of the inner sheath 1 and the outer sheath 2, the outer sheath 2 is sheathed at the outside of the inner sheath 1, and the outer sheath 2 has a hollow cylindrical structure; and the inner sheath 1 includes a straight cylindrical portion and a bell mouth portion, the bell mouth portion is used for sheathing an endoscope, and the bell mouth portion can play a guide role in a sheathing process; the straight cylindrical portion is disposed on a non-insertion end side of the inner sheath 1, the outside diameters of both ends of the inner sheath 1 are basically equal to the inside diameter of the outer sheath 2, and the inside diameter of the middle of the inner sheath 1 is less than the outside diameters of both ends of the inner sheath 1, so that a side wall of the inner sheath 1 protrudes toward the axial direction of the inner sheath 1, a hollow cavity is formed between the inner sheath 1 and the outer sheath 2, and the compressed waterproof jacket 3 can be placed in the hollow cavity. In the present invention, since the protective sheath is a disposable component, in order to reduce the production cost, the material of the inner sheath 1 and the outer sheath 2 is preferably hard plastic.

In the present invention, the waterproof jacket 3 has a tubular structure and is preferably a layer of transparent film, one end of the waterproof jacket 3 is fixedly sheathed on the inner sheath 1, and the other end of the waterproof jacket 3 can be pulled out from the hollow cavity, so that the waterproof jacket 3 compressed in the hollow cavity is pulled out from the waterproof jacket 3. Furthermore, the waterproof jacket 3 is mainly used for preventing dirt such as liquid from polluting an electric transmission line, so it is preferably made of a waterproof material. Furthermore, since the waterproof jacket 3 needs to be compressed in the hollow cavity between the inner sheath 1 and the outer sheath 2, the material of the waterproof jacket 3 should be as thin and soft as possible, so as to be conveniently compressed during the assembly. Furthermore, since the waterproof jacket 3 needs to be stretched each time in use, the waterproof jacket 3 also needs to have certain toughness. Therefore, in the present invention, materials such as polyethylene, polypropylene and polyvinyl chloride are preferably used as the material of the waterproof jacket 3.

Further, one end of the waterproof jacket 3 is fixed on an outer peripheral wall of the inner sheath 1, so it can be implemented in various implementation manners, for example, one end of the waterproof jacket 3 can be bonded to the outer peripheral wall of the inner sheath 1, an elastic device, such as a rubber band, can also be disposed at one end of the waterproof jacket 3, so that the waterproof jacket 3 is reliably sheathed at the outside of the inner sheath 1 during a stretching process without slipping off.

In the present invention, in order to insert the inner sheath 1 into the outer sheath 2 more conveniently in an assembly process, preferably, a plurality of grooves 11 are formed in the side wall of one side of the insertion end of the inner sheath 1, that is, a plurality of grooves 11 extending from the bell mouth portion to the straight cylindrical portion are formed in the side wall of the bell mouth portion, so that a plurality of elastic sheets 12 are formed on one side of the bell mouth portion of the inner sheath 1. The elastic sheets 12 can be deformed according to actual situations, such that the assembly is more convenient.

Preferably, the number of the elastic sheets 12 is an even number. Furthermore, in the present invention, two adjacent elastic sheets 12 are regarded as an elastic sheet group, one elastic sheet 12 in the elastic sheet group is formed with a protrusion 13 on an outer surface of the bell mouth portion, a groove is formed in a position corresponding to the protrusion 13 on an inner surface of the outer sheath 2, and when the inner sheath 1 is completely inserted into the outer sheath 2, the protrusion 13 is inserted into the groove. In the present invention, preferably, six elastic sheets are formed on the inner sheath 1, thereby not only ensuring the deformation ability of the elastic sheets, but also ensuring the strength of the elastic sheets to prevent breakage during the sheathing process.

Furthermore, in order to make the connection between the protective sheath and the endoscope such as the hysteroscope or the nephroscope more reliable and to prevent the protective sheath from falling off during the sheathing process, a connecting portion is formed on the other elastic sheet 12 in the elastic sheet group, the connecting portion is located at the boundary between the straight cylindrical portion and the bell mouth portion, and the connecting portion is a convex portion 14 protruding toward the axis of the inner sheath.

By disposing the protrusions 13 and the convex portions 14 on the elastic sheets 12 at intervals, the inner sheath 1 can be easily deformed elastically when it is sheathed with the outer sheath 2 or the endoscope, that is, when the inner sheath 1 is sheathed in the outer sheath 2, the elastic sheet 12 formed with the protrusion 13 on the outer surface in the elastic sheet group can be elastically deformed toward the axial direction of the inner sheath 1, that is, can contract into the inner sheath 1, thereby facilitating the clamping between the inner sheath 1 and the outer sheath 2.

When the inner sheath 1 needs to be sheathed on the endoscope, since a concave portion is disposed at a position corresponding to the convex portion 14 on the outer surface of the endoscope, after the inner sheath 1 is sheathed on the endoscope, the convex portion 14 can be clamped in the corresponding concave portion on the endoscope, at this time, since no protrusion 13 is disposed on the outer surface of the other elastic sheet 12 in the elastic sheet group, there is a certain space between the elastic sheet 12 and the outer sheath 2, the elastic sheet 12 formed with the convex portion 14 formed on the inner surface in the elastic sheet group can be elastically deformed toward the outer sheath 2, that is, can be expanded toward the outer sheath, thereby facilitating the sheathing of the inner sheath 1 and the self-locking quick connector endoscope, and the connection between the protective sheath and the endoscope is more reliable after the cooperation, and the protective sheath is unlikely to fall off.

Due to the settings in the above forms, no matter when the protective sheath is produced and assembled or is sheathed with the endoscope during use, the assembly process can be automatically simplified by elastic deformation and the efficiency is improved.

In the present invention, in order to make the cooperation between the inner sheath 1 and the outer sheath 2 more reliable, a circle of groove is formed in a position corresponding to the protrusion 13 on the inner surface of the outer sheath 2, when the inner sheath 1 is completely inserted into the outer sheath 2, the protrusion 13 can be clamped in the groove to increase the combination reliability between the inner sheath 1 and the outer sheath 2 and to prevent the inner sheath 1 and the outer sheath 2 from being accidentally separated.

Further, in order to prevent the protective sheath from falling off when being sheathed on the hysteroscope, preferably, a concave portion is disposed at a corresponding position on the outer surface of the endoscope, and the convex portion 14 can be clamped in the concave portion to improve the reliability of sheathing the waterproof jacket 3 at the outside of the endoscope.

Furthermore, as shown in FIG. 1-2 and FIG. 2-2, in order to further improve the sealing property between the sheathing of the protective sheath and the endoscope, and to prevent the liquid from flowing out between the protective sheath and the endoscope during surgery or inspection, preferably, the bell mouth portion of the inner sheath 1 is provided with an annular sealing ring 15 to cover the top of the bell mouth portion, so as to improve the sealing property and to prevent the liquid leakage.

In the present invention, since the waterproof jacket 3 needs to be pulled out from the hollow cavity between the inner sheath 1 and the outer sheath 2 during use, an unsealing portion 31 can be installed on the waterproof jacket 3, the unsealing portion 31 is fixedly connected with the waterproof jacket 3, and the waterproof jacket 3 can be pulled out from the hollow cavity by pulling the unsealing portion 31. The unsealing portion 31 can be a segment of sticker or patch connected with the waterproof jacket 3, or the unsealing portion 31 is not disposed separately, but apart of a pullable end of the waterproof jacket 3 extends out from the waterproof jacket 3 to conveniently pull out the waterproof jacket 3.

During specific implementation, the protective sheath is sheathed at the outside of the endoscope at first, and after the endoscope is connected with the electrical connecting line, the unsealing portion 31 or the waterproof jacket 3 that extends out from the protective sheath in advance is pulled to pull out the waterproof jacket 3 from the protective sheath to cover the electrical connecting line, so as to protect the electrical connecting line. After use, the shell is held and the protective sheath is separated from the endoscope with an external force to take off the protective sheath.

The protective sheath involved in the present invention has a simple structure, is convenient to use, effectively protects the electrical connecting line, completely avoids the situation that the electrical connecting line is polluted by pollutants, and also prevents the occurrence of a short circuit, thereby being safe and reliable.

Figure 3:
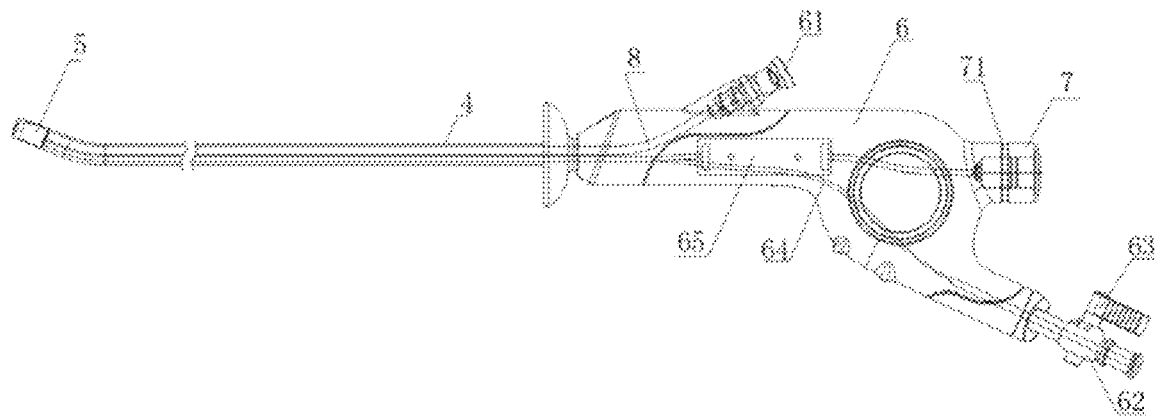
FIG. 3 is a schematic structural diagram of a hysteroscope of the present invention.
Figure 4:
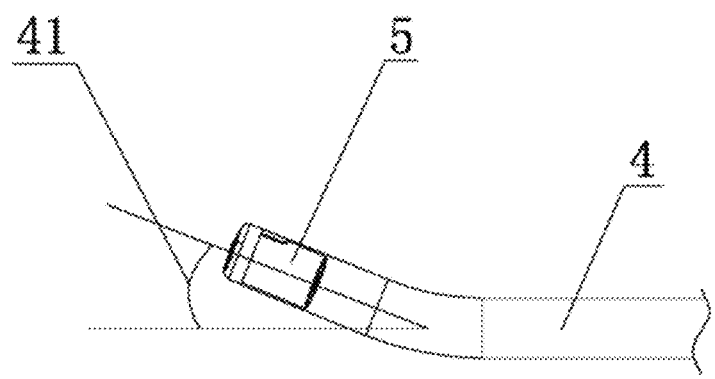
FIG. 4 is a schematic structural diagram of a third embodiment.

The present invention further provides a hysteroscope, as shown in FIG. 3, including an insertion tube 4 and a handle 6 connected with a non-insertion end of the insertion tube 4. In the present invention, as shown in FIG. 4, a bent portion is disposed at a position close to the insertion end of the insertion tube 4, so that the included angle between the axis of the insertion end of the insertion tube 4 and the axis of the non-insertion end of the insertion tube 4 is an acute angle 41, the acute angle 41 is preferably 15 degrees to 30 degrees, further, the acute angle 41 is preferably 25 degrees, 28 degrees or 30 degrees, when a doctor inspects a patient, the doctor only needs to rotate the hysteroscope slightly to inspect various parts of the uterus, thereby avoiding the situation that during the inspection of the patient, when the doctor needs to inspect the inner wall of the uterus, the doctor rotates the hysteroscope with the cervix as the fulcrum to hurt the cervix of the patient. Further, a camera module seat 5 is fixedly disposed at the insertion end of the insertion tube 4, the camera module seat 5 has a barrel-shaped structure, a camera module and a light source can be fixedly embedded in the camera module seat 5, and the camera module and the light source are electrically connected with a self-locking quick connector 7 disposed on the handle 6. In order to make the picture taken by the camera clearer, the camera is disposed on a top end face of the module seat; and the light source is preferably an LED light source, and the LED light source has the advantages of small volume, long service life, high brightness, low heat and the like, which further improves the efficiency of diagnosis and treatment and the accuracy of the diagnosis and treatment. However, the present invention is not limited to thereto, and any light emitting component that can emit light can be used as the light source, such as a light guide fiber, a light emitting diode, and the like. Further, one or more light sources can be provided, when multiple light sources are provided, the light sources are preferably disposed uniformly around the camera, and can be disposed on the end face of the camera module seat, and can also be disposed on the side wall of the camera module seat.

Further, after the camera and the light source are assembled in the camera module seat 5, the assembled camera module seat 5 can be regarded as a camera module, and in a production process, the assembled camera module can be directly assembled with the insertion tube 4, thereby improving the assembly efficiency.

Furthermore, in order to make the cooperation between the camera module and the insertion tube 4 more reliable, a buckle or other connection structures can be directly disposed on the shell of the camera module seat 5, and meanwhile, a corresponding bayonet or connection structure is disposed at a corresponding position of the insertion tube 4 to improve the reliability of the connection between the camera module and the insertion tube 4.

Figure 5:
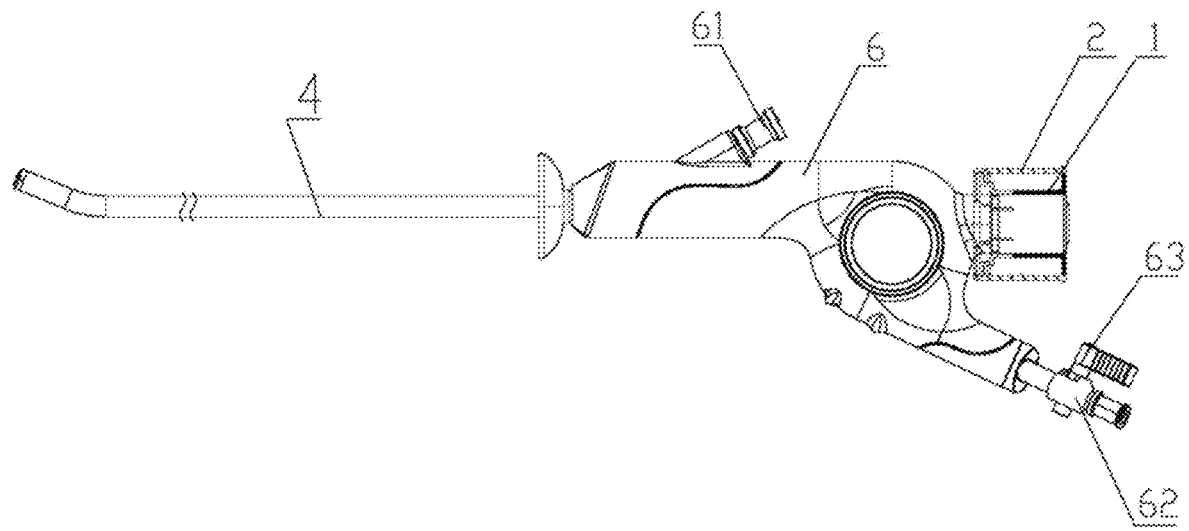
FIG. 5 is a schematic structural diagram after a protective sheath is sheathed with a hysteroscope.
Figure 6:
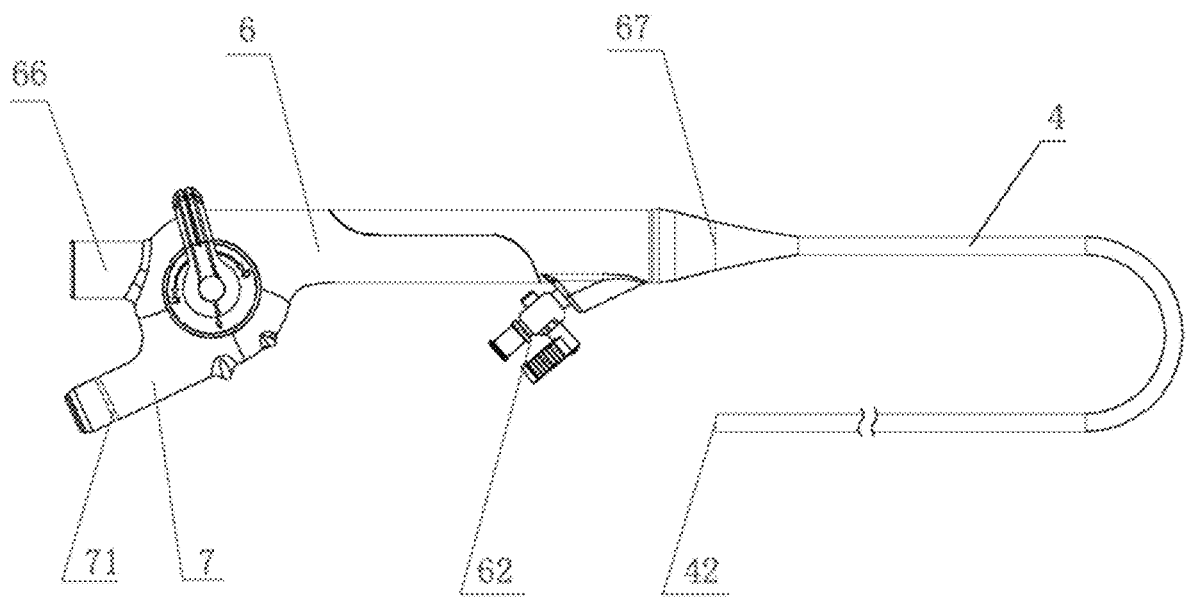
FIG. 6 is a schematic structural diagram of a nephroscope of the present invention.

In the present invention, in order to protect the electric transmission line connected with the self-locking quick connector 7 from being contaminated by water or other pollutants to cause accidents or damage, preferably, the protective sheath as described above (as shown in FIG. 5) is sheathed at the outside of the self-locking quick connector 7, and in order to make the connection there between more reliable, preferably, a concave portion 71 is disposed on the outer surface of the self-locking quick connector 7, the position of the concave portion 71 corresponds to the position of the convex portion 14 on the inner wall of the inner sheath 1 of the protective sheath after the two components are sheathed, after the protective sheath is installed in the self-locking quick connector 7, the convex portion 14 can be clamped in the concave portion 71, and the connection between the protective sheath and the self-locking quick connector 7 is more reliable.

In the present invention, the handle 6 preferably takes the shape of a gun, the handle 6 taking the shape of the gun can be gripped more easily, so that an operator is more comfortable to use the handle, and is more flexible to operate the handle. The handle 6 includes a connecting portion connected with the insertion tube 4 and a gripping portion, wherein the connecting portion corresponds to a bore portion of the gun, the gripping portion corresponds to a handle portion of the gun, in order to prevent the operator from accidentally sliding off or dropping off the hysteroscope during use, an anti-skid portion is preferably disposed on the gripping portion, and the position of the anti-skid portion is preferably disposed at the position corresponding to a trigger of the gun on the handle 6, so as to improve the use comfort and safety of the operator.

Furthermore, in the present invention, the handle 6 is preferably made of a low-cost non-metal material, such as a plastic material, thereby greatly reducing the production cost; at the same time, in the present invention, the insertion tube 4 is also preferably made of a non-metal material, therefore, the hysteroscope can be used as a disposable medical device without being sterilized before each use. In addition to greatly improving the efficiency of diagnosis and treatment, the safety factor of the diagnosis and treatment is also improved, and cross infection of patients during the inspection process can be effectively avoided.

Furthermore, in order to facilitate the assembly, in the present invention, the shell of the handle 6 is composed of two parts, that is, an upper shell and a lower shell, and connecting components that can cooperate with each other are disposed between the two parts, then the two parts can be assembled and closed after the assembly work is completed in the handle 6.

Preferably, the handle 6 is made of hard plastic, such as polytetrafluoroethylene (PTFE), polypropylene (PP), polyvinyl chloride (PVC), and the like, but the present invention is not limited to thereto, and various other non-metallic materials can also be adopted.

In the present invention, a water inlet base 62 and a water outlet base are disposed at a lower end of the gripping portion, the water inlet base 62 and the water outlet base are disposed at the rear lower side of the self-locking quick connector of the handle 6, that is, in actual operation, the water inlet base and the water outlet base are located at the rear of the operator, which can completely avoid the interference of a water tube externally connected with the water inlet base 62 and the water outlet base on the operator during use, and meanwhile can also avoid the interference on the patient; and valve switches 63 are respectively disposed on the water inlet base 62 and the water outlet base, so that water intake or drainage can be freely controlled according to the actual use needs, and meanwhile, the water intake amount or water discharge can also be conveniently adjusted. Further, a water inlet tube 64 is disposed in the water inlet base 62, a water outlet tube is disposed in the water outlet base, the water inlet tube 64 and the water outlet tube are two tube lines independent from each other, the water inlet tube 64 and the water outlet tube are both disposed in the insertion tube 4 and extend along the insertion tube 4, one end of the water inlet tube 64 and one end of the water outlet tube are both disposed on an end face of the insertion end of the camera module seat, and can also be disposed on the side wall of the insertion tube 4 close to the camera module seat, as long as it can be ensured that normal saline can be injected into the body of the patient or the blood turbid fluid that affects the definition of the camera in the body of the patient can be removed during a surgical process; and the other end of the water inlet tube 64 and the other end of the water outlet tube respectively communicate with the water inlet base 62 and the water outlet base, and the water discharge in the water inlet tube 64 and the water discharge in the water outlet tube can be respectively controlled by the respective valve switches 63, which respectively communicate with the same. Preferably, in the present invention, the inside diameters of the water inlet tube 64 and the water outlet tube are set as 1.1 mm-1.5 mm, preferably 1.2 mm or 1.3 mm, so as to meet the requirements for the water intake amount or the water discharge during the surgical process.

Further, in order to enable the operator to perform treatment while inspecting the patient, the upper end of the connecting portion is provided with a first instrument mouth 61 at a position close to the insertion tube 4 for the entry and exit of a medical instrument. In the present invention, the first instrument mouth 61 is disposed directly in front of the operator and is located above the handle 6, which is more in line with the operation convenience of the operator during use; at the same time, a first instrument tube 8 is further disposed in the insertion tube 4, an instrument outlet of the first instrument tube 8 is disposed on the end face of the insertion end of the camera module seat, an instrument inlet of the first instrument tube 8 communicates with the first instrument mouth 61, and during use, the operator can use the first instrument mouth 61 and the first instrument tube 8 to convey the medical instrument into the body of the patient to treat the patient.

In the present invention, the insertion tube 4 is made of a metal material, for example, stainless steel (such as SUS304), according to different use needs, a soft hose made of a non-metal material or the like can be used as the insertion tube 4, such as a polyurethane tube (PU tube) or a thermoplastic polyurethane elastomer rubber tube (TPU tube) and so on. However, the present invention is not limited to thereto, and tubes of other materials can also be selected as the insertion tube 4 according to the use needs.

During an actual diagnosis and treatment process, it is often necessary to use two or more medical instruments, so a second instrument tube is also disposed in the insertion tube 4, the second instrument tube is preferably disposed below the first instrument tube 8, a second instrument mouth is disposed on the handle 6, a second instrument mouth waterproof plug is sheathed at the outside of the second instrument mouth, and the second instrument mouth is preferably disposed at the upper end of the connecting portion of the handle 6 and is preferably disposed with the first instrument mouth 61 side by side to facilitate the use of the doctor; and the instrument outlet of the second instrument tube is disposed on the end face of the insertion end of the camera module seat 6, and the instrument inlet of the second instrument tube communicates with the second instrument mouth. In the present embodiment, the separately disposed second instrument tube enables the doctor to use two medical instruments to treat the patient at the same time during use, and the operation is more convenient.

In the present invention, a printed circuit board 65 (PCB) is preferably disposed in the handle 6, and the camera, the light source, the printed circuit board 65 and the self-locking quick connector 7 are connected by electrical connecting lines in sequence. The camera and light source are connected with the self-locking quick connector 7 through the PCB, in this way, the length and the number of the electrical connecting lines in the handle 6 can be effectively reduced, the diameter of the insertion tube 4 is further reduced, and the conversion of the core numbers of the electrical connecting lines can also be realized, for example, in a preferred embodiment of the present invention, the camera is preferably connected to the PCB by using a multi-core shielding line, while the PCB and the self-locking quick connector 7 are connected by a multi-core shielding line, therefore the self-locking quick connector 7 has a wider universal range and greater applicability.

Furthermore, the self-locking quick connector 7 is disposed directly behind the handle 6 to prevent the transmission line from causing inconvenience to the operator during the inspection process and to improve efficiency of diagnosis and treatment.

The hysteroscope involved in the present invention can effectively prevent dirt or other liquid from contaminating the electric transmission line, so as to prevent short circuit and other situations, thereby being safe and reliable.

The present invention further discloses a nephroscope, including an insertion tube 4 and a handle 6 connected with a non-insertion end of the insertion tube 4, a tip head 42 is fixedly disposed at a front end of the insertion tube 4, and the tip head 42 is provided with an instrument tube mounting channel for inserting an instrument tube and a camera module mounting channel for mounting a camera module; the handle 6 is connected to a tail end of the insertion tube 4 through a rigid connecting piece 67, a rear end of the handle 6 is provided with a self-locking quick connector 7 for connecting a display device, and the protective sheath as described above is sheathed at the outside of the self-locking quick connector 7; and wherein, a front end face of the tip head 42 of the insertion tube 4 is provided with an instrument outlet, a rear end face of the handle 6 is provided with a corresponding instrument inlet, the instrument inlet is inserted into the handle 6 to communicate with an instrument tube in the insertion tube 4, an acute included angle between the section axis of the instrument inlet and the section axis of an instrument catheter in the handle 6 is less than 5 degrees, or is less than 8 degrees, or is less than 10 degrees, or is less than 15 degrees.

Further, the front end face of the tip head 42 is further provided with a water outlet, the water inlet base 62 is disposed at the lower end of the handle 6, the water inlet base 62 communicates with the water outlet through a water inlet tube that is inserted into the handle and the inner cavity of the insertion tube 4, the water inlet tube is separated from the instrument tube, or the water inlet tube and the instrument tube share a conduit. When extravasated blood is attached to the camera or the inner wall of a human body cavity, the liquid in the cavity is turbid, which reduces the visibility; or when gravels and other obstacles hinder the camera, water can be injected into the human body through the water inlet tube, the water flows into the human body from the water outlet to flush away the extravasated blood, the turbid liquid or the gravels, so that the camera can clearly observe the situation on the inner wall of the human body cavity, if the water pressure is too high or after stone breakage is completed, negative pressure suction drainage can be performed through a channel between the insertion tube 4 and the outer sheath of a ureter nephroscope, in order to discharge excess water or stones from the human body.

In the present invention, in order to protect the electric transmission line connected with the self-locking quick connector 7 from being contaminated by water or other pollutants to cause accidents or damage, preferably, the protective sheath as described above (as shown in FIG. 5) is sheathed at the outside of the self-locking quick connector 7, and in order to make the connection there between more reliable, preferably, a concave portion 71 is disposed on the outer surface of the self-locking quick connector 7, the position of the concave portion 71 corresponds to the position of the convex portion 14 on the inner wall of the inner sheath 1 of the protective sheath after the two components are sheathed, after the protective sheath is installed in the self-locking quick connector 7, the convex portion 14 can be clamped in the concave portion 71, and the connection between the protective sheath and the self-locking quick connector 7 is more reliable.

The nephroscope involved in the present invention can effectively prevent dirt or other liquid from contaminating the electric transmission line to prevent short circuit and other situations, thereby being safe and reliable.

The present invention further discloses a use method of the protective sheath, including the following steps:

step 1: making the insertion end of the protective sheath face to the self-locking quick connector 7 of the hysteroscope or the nephroscope, and sheathing the same at the outside of the self-locking quick connector 7, until the connecting portion is clamped with the self-locking quick connector 7;

step 2: forming a plugging connection between an electric transmission line and the self-locking quick connector 7; and step 3: holding the unsealing portion 31 to pull out the waterproof jacket 3 to cover the electric transmission line.

In summary, the protective sheath involved in the present invention is simple in structure and convenient to use, and can prevent the dirt or other liquid from contaminating the electric connecting lines to prevent short circuit and other situations, thereby being safe and reliable; and further, the protective sheath has a low production cost and can be used as a disposable medical device, thereby generating no economic pressure on the patient. In addition, the hysteroscope with the protective sheath involved in the present invention can treat the patient in time while performing routine examination on the uterus of the patient, thereby being convenient and safe; and at the same time, it can also effectively prevent the electrical connecting lines from being contaminated by the dirt to generate short circuit and other situations, thereby being safe and sanitary and worthy of extensive promotion and application.

The above embodiments merely illustrate the principle of the present invention and its effects, but are not intended to limit the present invention. Any skilled in the art can modify or change the above embodiments without departing from the spirit and scope of the present invention. Therefore, all equivalent modifications or changes made by those skilled in the art without departing from the spirit and technical ideas disclosed by the present invention should still be encompassed by the claims of the present invention.

The invention claimed is:

1. A protective sheath, comprising:
   an inner sheath and an outer sheath, which are sleeved together,
   wherein the outer sheath has a cylindrical structure,
   the inner sheath comprises:
   a straight cylindrical portion;
   a bell mouth portion, wherein the bell mouth portion is located on an insertion end side of the inner sheath, a side wall of the bell mouth portion is provided with a plurality of grooves extending from the bell mouth portion to the straight cylindrical portion; and
   a plurality of elastic sheets formed at the insertion end side of the inner sheath;
   wherein the straight cylindrical portion is located on a non-insertion end side of the inner sheath;
   a connecting portion formed on an inner wall of each of the plurality of elastic sheets,
   wherein a hollow cavity is disposed between the inner sheath and the outer sheath, and a compressed waterproof jacket is disposed in the hollow cavity, the waterproof jacket has a tubular structure, one end of the waterproof jacket is fixedly sheathed on the inner sheath, an other end of the waterproof jacket can be pulled out from a non-insertion end of the protective sheath, so that the waterproof jacket is pulled out from the hollow cavity.

2. The protective sheath according to claim 1, wherein a number of the plurality of elastic sheets is an even number.

3. The protective sheath according to claim 2, wherein two adjacent elastic sheets are regarded as an elastic sheet group, one elastic sheet in the elastic sheet group is formed with a protrusion on an outer surface of the bell mouth portion, a groove is formed in a position corresponding to the protrusion on an inner surface of the outer sheath, and when the inner sheath is completely sheathed in the outer sheath, the protrusion is inserted into the groove.

4. The protective sheath according to claim 3, wherein the connecting portion is formed on the other elastic sheet in the elastic sheet group, the connecting portion is located at the boundary between the straight cylindrical portion and the bell mouth portion, and the connecting portion is a convex portion protruding toward the axis of the inner sheath.

5. The protective sheath according to claim 1, wherein one end of the waterproof jacket is fixed at the non-insertion end of the inner sheath.

6. The protective sheath according to claim 1, wherein the bell mouth portion of the inner sheath is provided with an annular sealing ring to cover the top of the bell mouth portion.

7. The protective sheath according to claim 1, wherein the protective sheath is provided with an unsealing portion, and the unsealing portion is fixedly connected with the waterproof jacket.

8. A hysteroscope, comprising:
an insertion tube; and
a handle connected with a non-insertion end of the insertion tube,
wherein a camera module seat is fixedly disposed at an insertion end of the insertion tube, a camera and a light source are disposed in the camera module seat, and the camera and the light source are electrically connected with a self-locking quick connector disposed on the handle, and the protective sheath according to claim 1 is sheathed at an outside of the self-locking quick connector;
the handle takes the shape of a gun, the handle comprises:
a connecting portion connected with the insertion tube;
a gripping portion;
a first instrument mouth disposed at an upper end of the connecting portion;
a water inlet base and a water outlet base are disposed at a lower end of the gripping portion;
valve switches respectively disposed on the water inlet base and the water outlet base;
a water inlet tube disposed in the water inlet base;
a water outlet tube disposed in the water outlet base, wherein the water inlet tube and the water outlet tube are both disposed in the insertion tube and extend along the insertion tube, one end of the water inlet tube and one end of the water outlet tube are both disposed on an end face of the insertion end of the camera module seat, and an other end of the water inlet tube and an other end of the water outlet tube respectively communicate with the water inlet base and the water outlet base; and a first instrument tube disposed in the insertion tube;
an instrument outlet of the first instrument tube disposed on the end face of the insertion end of the camera module seat, and an instrument inlet of the first instrument tube communicating with the first instrument mouth; and
a water retaining ring sheathed at an outside of the non-insertion end of the insertion tube, wherein the water retaining ring moves along an axis of the insertion tube.

9. The hysteroscope according to claim 8, wherein a convex portion is formed on an inner wall of the inner sheath of the protective sheath, a concave portion is disposed at a corresponding position on an outer surface of the self-locking quick connector, and the convex portion is clamped in the concave portion.

10. The hysteroscope according to claim 8, wherein a number of the plurality of elastic sheets is an even number.

11. The hysteroscope according to claim 10, wherein two adjacent elastic sheets are regarded as an elastic sheet group, one elastic sheet in the elastic sheet group is formed with a protrusion on an outer surface of the bell mouth portion, a groove is formed in a position corresponding to the protrusion on an inner surface of the outer sheath, and when the inner sheath is completely sheathed in the outer sheath, the protrusion is inserted into the groove.

12. The hysteroscope according to claim 11, wherein the connecting portion is formed on the other elastic sheet in the elastic sheet group, the connecting portion is located at the boundary between the straight cylindrical portion and the bell mouth portion, and the connecting portion is a convex portion protruding toward the axis of the inner sheath.

13. The hysteroscope according to claim 8, wherein one end of the waterproof jacket is fixed at the non-insertion end of the inner sheath.

14. The hysteroscope according to claim 8, wherein the bell mouth portion of the inner sheath is provided with an annular sealing ring to cover the top of the bell mouth portion.

15. The hysteroscope according to claim 8, wherein the protective sheath is provided with an unsealing portion, and the unsealing portion is fixedly connected with the waterproof jacket.

16. A nephroscope, comprising:
an insertion tube; and
a handle connected with a non-insertion end of the insertion tube; and
a tip head fixedly disposed at a front end of the insertion tube,
wherein the tip head is provided with an instrument tube mounting channel for inserting an instrument tube and a camera module mounting channel for mounting a camera module; the handle is connected to a tail end of the insertion tube through a rigid connecting piece, a rear end of the handle is provided with a self-locking quick connector for connecting a display device, and the protective sheath according to claim 1 is sheathed at an outside of the self-locking quick connector; and
wherein, a front end face of the tip head of the insertion tube is provided with an instrument outlet, a rear end face of the handle is provided with a corresponding instrument inlet, the instrument inlet is inserted into the handle to communicate with an instrument tube in the insertion tube, an acute included angle between the section axis of the instrument inlet and the section axis of an instrument catheter in the handle is less than 15 degrees.

17. The nephroscope according to claim 16, wherein a convex portion is formed on an inner wall of the inner sheath of the protective sheath, a concave portion is disposed at a corresponding position on an outer surface of the self-locking quick connector, and the convex portion can be clamped in the concave portion.

18. The nephroscope according to claim 16, wherein a number of the elastic sheets is an even number.

19. The nephroscope according to claim 18, wherein two adjacent elastic sheets are regarded as an elastic sheet group, one elastic sheet in the elastic sheet group is formed with a protrusion on an outer surface of the bell mouth portion, a groove is formed in a position corresponding to the protrusion on an inner surface of the outer sheath, and when the inner sheath is completely sheathed in the outer sheath, the protrusion is inserted into the groove.

20. The nephroscope according to claim 19, wherein the connecting portion is formed on the other elastic sheet in the elastic sheet group, the connecting portion is located at the boundary between the straight cylindrical portion and the bell mouth portion, and the connecting portion is a convex portion protruding toward the axis of the inner sheath.

21. The nephroscope according to claim 10, wherein one end of the waterproof jacket is fixed at the non-insertion end of the inner sheath.

22. The nephroscope according to claim 10, wherein the bell mouth portion of the inner sheath is provided with an annular sealing ring to cover the top of the bell mouth portion.

23. The nephroscope according to claim 10, wherein the protective sheath is provided with an unsealing portion, and the unsealing portion is fixedly connected with the waterproof jacket.

* * * * *